Oct. 6, 1942. C. L. CANUP Plant Pat. 547
CARNATION
Filed April 18, 1942
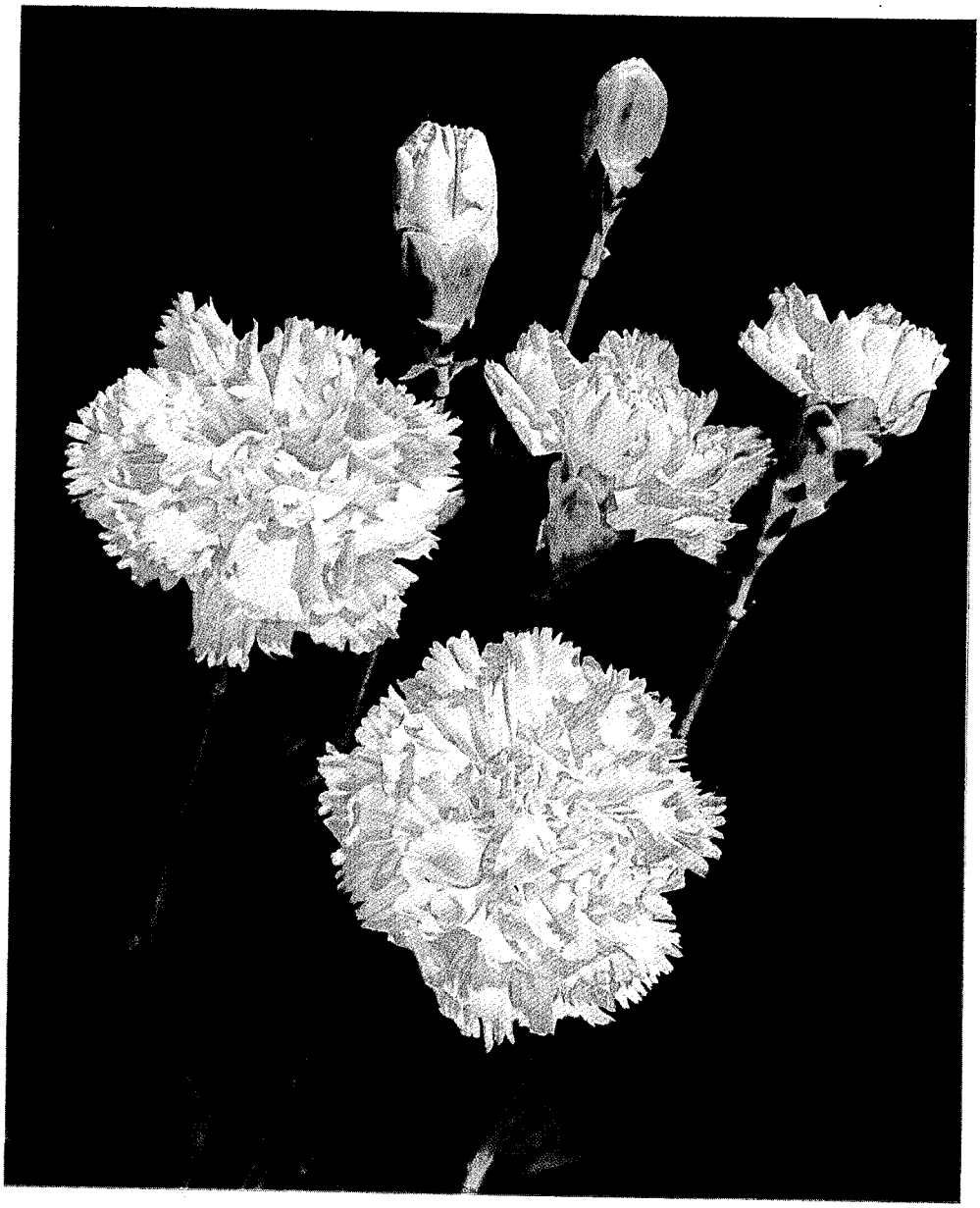
INVENTOR
Calvin L. Canup
By Orville M. Kile
Plant Pat Agt.

Patented Oct. 6, 1942

Plant Pat. 547

UNITED STATES PATENT OFFICE

547

CARNATION

Calvin L. Canup, Knoxville, Tenn., assignor to Baum's Home of Flowers, Inc., Knoxville, Tenn.

Application April 18, 1942, Serial No. 439,603

1 Claim. (Cl. 47—60)

My present invention relates to a new variety of carnation of the greenhouse forcing type. The particular object of my invention is to produce a new and improved variety of deep pink or rose colored carnation which is prolific both in blooms and in reproduction, having large blooms that do not fade but are tough and long-lasting.

My new variety resulted from a cross between Patrician and an unnamed seedling which in turn resulted from a series of seedling crosses. These breeding efforts were carried on by me and others at the Baum greenhouses in Knoxville, Tennessee. The final cross which produced this variety was made by me.

I have observed and asexually reproduced this new variety for several years and the novel characteristics have proved to be permanently fixed. The plant and blooms are particularly tough and strong and the blooms last about twice as long as those of most other carnation varieties. These features make the new variety an excellent shipper.

The original illustrations making up a part of this application show several specimens of the bloom of this new variety in various stages of opening, together with some of the stems and foliage. In the original illustrations these are shown in slightly less than natural size, and in as near natural colors as it was possible for the artist to portray them. However, in an effort to show the lights and shadows, the artist somewhat deepened the color in places and highlighted it in others, thus detracting to some extent from the true impression of evenness of coloring.

Following is a detailed description of the plant and blossom of this new variety. Color plate references indicate Ridgway's Color Standards and Nomenclature. Where color plate references are not given, the ordinary dictionary meaning of the term is intended.

*The plant*

Growth habits: The plant of this variety is a very vigorous grower, throwing an abundance of shoots to be used for cuttings. Because of these features it is a rapid reproducer. The plant is apparently free from all diseases and insects which commonly affect carnations, since it has been grown in greenhouses with infected and infested plants of other carnation varieties yet has never been affected.

Blooming habits: This new variety is a very prolific bloomer, producing an unusually good percentage of very large, perfect blooms.

Stems: Long, wiry, strong.

*Color.*—The general color effect is approximately Russian Green (pl. XLII). Actually the color is Dark Dull Yellow Green (Pl. XXXII), overlaid with a heavy bloom of Deep Glaucous Gray (Pl. XLVII).

Foliage: Medium in width and length. Average in amount. Tightly curled on upper portion of stem. Color about the same as the stems, with overlay heavier on tips.

Calyx: Very broad, in the open flower measuring 1¼ to 1½ inches across at its widest point. Consists of a single tube with five or six points. Of the blooms observed about half showed a calyx with six points—an unusual feature in carnations. Calyx is very tough, heavy and strong; never known to split. As the flower opens, the calyx tips form unusually high bulges which allow for some expansion of the flower without splitting the calyx. The color of the calyx is Lumere Green (Pl. XVII) at the base, to Light Bice Green (Pl. XVII) at its broadest portion, overlaid with a dusty bloom of Pistachio Green (Pl. XII) on the upper portion.

Bracts: Strong; deep; same color as calyx but with darker tips.

*The flower*

Bud:

*Shape.*—Long but blunt at end.

*Size.*—Just before opening, the bud measures approximately 1½ inches in length.

*Opening.*—Slow.

*Color.*—Approximately Spinel Pink (Pl. XXVI). The inner surface of the newly opened bud is approximately Tyrian Rose (Pl. XII) although slightly lighter in tone.

Blossom:

*Size.*—Very large, measuring 3½ to 4 inches in diameter when grown under ordinary greenhouse conditions.

*Form.*—Very full; irregular; center rather low; petals crinkled only slightly and individually distinguished.

*Petalage.*—Average number of petals in February is sixty.

*Fragrance.*—Slight. Less than is noted in the usual large carnation.

Petals:

*Size.*—Outer petals measure 1⅜ inches wide and up to 2½ inches long including shank.

*Shape.*—General shape of the colored portion of the petal shows it slightly broader than the vertical measurement. Edge very irregular, sometimes deeply cut; only slightly wavy.

*Texture.*—Heavy and very substantial.

*Color.*—A bright, clear, deep pink to rose color, uniformly spread over the entire surface of the petals. It is very difficult to describe this color by comparison with the available color standards. The nearest color found in Ridgway's Color Standards and Nomenclature lies between Spinel Pink (Pl. XXVI) and Rose Red (Pl. XII). There is no trace of purple in the color which remains unfaded with age. The reverse side of the flower petals is lighter, being approximately Spinel Pink (Pl. XXVI).

Reproductive organs:

*Stamens.*—White; few; short and without anthers.

*Pistils.*—Usually two; straight; white; approximately 1⅜ inches long; seldom show in open flowers.

*Ovary.*—Very small for so large a flower. Contains many ovules.

Having thus disclosed my invention, I claim:

The new and distinct variety of carnation herein shown and described, characterized particularly by its rapid propagation, its high degree of resistance to diseases and insects common to carnations; its strong, long, wiry stems; and its prolific production of very large, well-formed blossoms having tough non-splitting calyx, unfading bright pink to rose color, and unusually good lasting qualities.

CALVIN L. CANUP.